United States Patent [19]

Merrick et al.

[11] Patent Number: 5,534,121
[45] Date of Patent: Jul. 9, 1996

[54] PREPARATIVE TWO DIMENSIONAL GEL ELECTROPHORESIS SYSTEM

[75] Inventors: B. Alex Merrick, Cary; Rachel M. Patterson, Chapel Hill; Robert G. Hall; Chaoying He, both of Durham; James K. Selkirk, Chapel Hill, all of N.C.

[73] Assignee: The United States of America as represented by the Department of Health and Human Services, Washington, D.C.

[21] Appl. No.: 243,643

[22] Filed: May 16, 1994

[51] Int. Cl.⁶ .................. G01N 27/26; G01N 27/447
[52] U.S. Cl. .................. 204/459; 204/462; 204/465; 204/610; 204/613; 204/615
[58] Field of Search .................. 204/180.1, 182.1, 204/182.8, 299 R

[56] References Cited

U.S. PATENT DOCUMENTS

| | | | |
|---|---|---|---|
| 4,284,491 | 8/1981 | Vesterberg | 204/299 R |
| 4,416,761 | 11/1983 | Brown et al. | 204/182.8 |
| 4,481,094 | 11/1984 | Fernandez de Castro | 204/182.8 |
| 4,483,885 | 11/1984 | Chait et al. | 427/58 |
| 4,824,547 | 4/1989 | Zhang et al. | 204/299 R |
| 4,840,714 | 6/1989 | Littlehales | 204/180.1 |
| 4,874,490 | 10/1989 | Hochstrasser | 204/182.1 |
| 5,027,018 | 6/1991 | Kindlmann et al. | 204/182.8 |
| 5,160,594 | 11/1992 | Huff et al. | 204/182.9 |
| 5,284,559 | 2/1994 | Lim et al. | 204/182.8 |
| 5,292,420 | 3/1994 | Nakanura | 204/299 R |

OTHER PUBLICATIONS

Two–Dimensional Gel Electrophoresis by D. Rickwood et al. pp. 234–272.
Bio–Rad Life Science Research Products 1995 p. 164.

*Primary Examiner*—John Niebling
*Attorney, Agent, or Firm*—Lowe, Price, LeBlanc & Becker

[57] ABSTRACT

A preparative two dimensional gel electrophoresis system which serves as a single procedure for separation and isolation of preparative amounts of proteins from complex biological preparations. The system includes sized-up isoelectric focusing tube gels and slab gel molds which allow for sample loads of between about 0.5 and 2 mg or greater. Increased protein loads, resolution and electrotransfer allow for subsequent sequencing of separated proteins by conventional methods.

10 Claims, 10 Drawing Sheets

PLC-α
AA SEQ                              SDVLELTDENFESRXXD
                                    ||||||||||||||| |
cDNA            MPSAALRCSRAWRLLLASALLASASDVLELTDENFESRVSDTGSA...

α -TUBULIN
AA SEQUENCE     MREXISIHVGQAXV
                ||| ||||||||| |
cDNA            MRECISIHVGQAGVQIGNACWE...

GRP 78
AA SEQUENCE                   EEEDKKEDVGTVVGIDL
                              |||||||||||||||||
cDNA            MKFTVVAAALLLLCAVRAEEEDKKEDVGTVVGIDLGTTYS...

GRP 75
AA SEQUENCE                          ASEAIKGAVVGIDLGTTNSXVAVM
                                     |||||||||||||||||||| ||||
cDNA            ...NGLSHEAFRFVSRRDYASEAIKGAVVGIDLGTTNSCVAVMEGKQAK...

HSP-65
AA SEQUENCE                             AKDVKFGADARALMLQGVDLL
                                        |||||||||||||||||||||
cDNA            MLRLPTVFRQMRPVSRVLAPHLTRAYAKDVKFGADARALMLQGVDLLADAVA...

NAGAT
AA SEQUENCE                  HALRPXILXXXMLV
                             ||||| ||   |||
cDNA            MAEVLRTLAGKPKCHALRPMILFLIMLVLVLFGY...

VIMENTIN
AA SEQUENCE                 SSVPGVRLLQDSVDFSLADA
                            ||||||||||||||||||||
cDNA            ...AYVTRSSAVRLRSSVPGVRLLQDSVDFSLADAINTEF...

GELSOLIN
AA SEQUENCE     VVENPEFLKAGKEPGLQXXRVEK
                |||||||||||||||||  ||||
cDNA            MVVENPEFLKAGKEPGLQIWRVEKFPLV...

FIG.7A

```
CALRETICULIN
AA SEQUENCE                         DPAIYFKEQFLDGDAXTNRXV
                                    ||||||||||||| ||| |
cDNA               MLLSVPLLLGLLGLAAADPAIYFKEQFLDGDAWTNRWVESKHK...

RETICULOCALBIN
AA SEQUENCE                             GPTVRKERVVIPDDEE
                                        |||||||||| || |
cDNA               MARGGRLGLALGLLLALVLALRAKPTVRKERVVRPDSELGERPPE...
```

PREPARATIVE TWO DIMENSIONAL GEL ELECTROPHORESIS SYSTEM

TECHNICAL FIELD

The present invention relates to methods and procedures for separating and isolating proteins from complex biological preparations.

BACKGROUND ART

Automated protein sequencing has become increasingly sensitive and compatible for analysis of blotted proteins. Vertical flow, blot cartridges in protein sequencers produce usable sequence information at the 10–20 pmole range which amounts to 0.5–1 µg for a 50 kDa protein. Despite the increasing sensitivity of newer sequencing instruments, the isolation of unknown proteins often presents a technical challenge, particularly when only protein mass is known and specific antibodies or affinity ligands are unavailable.

The separation power of two dimensional polyacrylamide gel electrophoresis (2-D PAGE) has often been exploited as part of isolation schemes for determining the amino acid sequence of unknown proteins from complex protein mixtures. Proteins are usually elecrotransferred to inert membranes, detected with reversible stains which do not interfere with Edman degradative chemistries, excised and sequenced. Several purification procedures incorporate 2-D PAGE for protein isolation and sequencing. A common approach involves partial purification of the desired protein using any number of chromatographic methods, which commonly include molecular sieving, ion exchange and ligand- or immunoaffinity purification prior to 2-D PAGE as a final purification step. However, these methods involve extensive sample preparation and multi-step procedures which often rely upon following a known biological activity of the protein or adding trace amount of purified protein during the fractionation process.

Another strategy is to combine individual proteins from multiple, high-resolution 2-D PAGE isolation under analytical conditions ($\leq$100 µg load). For example, Bauw et al (*J. Electrophoresis*, 1990 11, 528–536) pooled individual Coomassie Brilliant Blue (CBB)-stained proteins from 15–20 analytical 2-D PAGE gels into a single well for sodium dodecyl sulfate polyacrylamide gel electrophoresis (SDS PAGE). Each protein was electroeluted from multiple, 2-D PAGE gel punches into a single band during SDS-PAGE, electroblotted onto PVDF, stained and sequenced. However, the low sensitivity of reversible stains which do not interfere with sequence makes detection difficult for low abundance proteins. Such proteins in low concentrations are often only visible with sensitive metal stains or radiolabel. Also, protein loss during sample consolidation frequently limits the effectiveness of protein pooling for sequencing from multiple 2-D PAGE gels.

A third approach involves detection of critical protein changes by analytical 2-D PAGE and scale-up to preparative 2-D PAGE for isolation of sufficiently quantities of protein desired from sequencing. This approach has recently been used for sequencing two isoforms of phospholipase C-α induced by estrogen treatment or serum-induced proliferation (Mobbs et al., *Science* 1990, 247, 1477–1479; Merrice et al. *Biochem. Arch.* 1993, 9, 335–340). Another group has used preparative 2-D PAGE to sequence proteins from bacterial ribosomes and the postsynaptic density of bovine brain (Walsh et al, *Biochemistry* 1988, 27, 6867–6876; Walsh et al. *J. Neurochem.* 1992, 59, 667–678). These studies indicate the potential of preparative 2-D PAGE in identifying proteins perturbed by experimental treatment or those proteins which are selectively expressed in specific tissues.

At the present time, commercial devices for analytical 2-D PAGE are not readily adaptable for preparative sample loads from complex protein preparations in the milligram range. Although several preparative isoelectric focusing devices are available and have high sample capacity, they function as stand-alone units which are not immediately integrated into additional systems for final protein resolution and electrotransfer.

Strategies are needed for rapid protein isolation in order to identify disease-related proteins and facilitate the design of oligonucleotides for further molecular inquiry.

DISCLOSURE OF THE INVENTION

It is accordingly one object of the present invention to provide a preparative two dimensional gel electrophoresis system which serves as a single procedure for separation and isolation of preparative amounts of proteins from complex biological preparations.

Another object of the present invention is to provide a two dimensional gel electrophoresis system which is capable of isolating individual proteins in sufficient quantity for amino-terminal sequencing after a single run.

A further object of the present invention is to provide a two dimensional gel electrophoresis system and procedures for use thereof which optimize protein load, resolution and electrotransfer.

According to these and further objects of the present invention which will become apparent as description thereof proceeds, the present invention provides a method for separating complex protein mixtures which involves the steps of:

a) prefocusing an isoelectric focusing tube gel for a period of time sufficient to produce a linear pH gradient through the isoelectric focusing tube gel;

b) loading the prefocused isoelectric focusing tube gel with a sample mixture of proteins;

c) applying a voltage across the sample-loaded isoelectric tube to cause separation of the sample mixture along a first direction;

d) transferring the electrophoresed sample mixture from step c) to a slab gel; and e) applying a voltage across the slab gel to cause separation of the sample mixture along a second direction.

The present invention also provides for an improvement over known two dimensional gel electrophoresis processes which involves:

prefocusing isoelectric tube gels for a period of time sufficient to produce a linear pH gradient through the isoelectric focusing tube gels; and loading the prefocused isoelectric tube gels with between about 0.5 to 2 mg of a sample mixture of proteins.

The present invention further provides for an improvement over known two dimensional gel electrophoresis apparatus which includes;

a plurality of isoelectric focusing tube gels having lengths of about 22 cm and inside diameters of about 6 mm; and a plurality of slab gel molds having dimensions of 20×25 cm.

BRIEF DESCRIPTION OF DRAWINGS

The present invention will be described with reference to the attached drawings which are given by way of non-limiting examples only, in which.

BEST MODE FOR CARRYING OUT THE INVENTION

The present invention is directed to a preparative two dimensional gel electrophoresis system which serves as a single procedure for separation and isolation of preparative amounts of proteins from complex biological preparations. The system (herein referred to as a "preparative 2-D PAGE" system) includes a preparative isoelectric focusing device to separate proteins by charge, a glass mold for use in preparative polyacrylamide gel separation of proteins by mass, and operating procedures for use. Separation and isolation of preparative amounts of protein have wide utility in biological research. A particular need addressed by the preparative 2-D PAGE system of the present invention is isolation of individual proteins in sufficient quantity for amino-terminal sequencing after a single run.

The present invention involves specific devices, procedures and conditions which have been developed in order to optimize protein load, resolution and electrotransfer. The present invention has been used in the preparative 2-D PAGE isolation of major cytoplasmic proteins from C3H10T1/2 fibroblasts in amounts sufficient for sequencing. The effectiveness of the present invention has been evaluated by comparing protein sequences obtained by the present invention to those in automated databases for identification. In addition, the present invention has been used to discover new proteins which have not been reported to be synthesized in C3H10T1/2 cells.

Based upon the finding that C3H10T1/2 murine fibroblasts express a variety of proteins in various subcellular fractions which are relevant to experimental transformation and carcinogenesis, preparative 2-D PAGE procedures according to the present invention were developed to identify major cytoplasmic proteins by electroblotting and microsequencing. Isoelectric focusing tube gels were enlarged to 6 mm ID to accommodate larger protein loads at 0.5 to 2 mg protein. Separated proteins were electrotransferred from 6 mm thick slab gels onto $0.22\mu$ polyvinylidene difluoride membranes. Nearly 100 prominent blotted proteins were stained with CBB between isoelectric point (pI) 4.5–7.0 and 18–106 kDa and, of these, 27 prominent and well-resolved proteins were selected from sequencing. Sequences of 14 to 24 amino acid residues in length were obtained from 11 proteins which were identified from computerized databases. Some of these identified proteins had structural or enzymatic functions while others had only recently been discovered, including a newly reported Hsp 70 class member and a novel calcium-binding protein, reticulocalbin. The new heat shock protein has a molecular mass of 75 kDa and has been designated as glusoce regulated protein 75 (Grp75), PBP74, CSA or $p66^{mot-1}$ in mice and humans with purported roles in transformation and antigen processing. Reticulocalbin is an endoplasmic reticular protein which contains six domains of the EF-hand motif associated with high-affinity calcium-binding proteins. It may be involved in protein transport and luminal protein processing. In addition, sequences of 5 to 11 residues in length were also obtained from six other unidentified protein. Thus, it has been found that preparative 2-D PAGE serves as a powerful one-step purification method for protein isolation and characterization from an important in vitro murine model for the study of carcinogenesis.

During the course of the present invention, methodology and devices were developed for preparative 2-D PAGE to accommodate milligram loads of complex protein preparations in order to obtain sufficient amounts of blotted protein for microsequencing. Although many preparative isoelectric focusing (IEF) or SDS-PAGE units are available, they function as stand-alone units and require considerable prepurification procedures before sample application. The use of centrifugal isolates provides a procedurally simple means for protein enrichment of subcellular compartments before preparative protein separation and can be extended to mitochondrial, endoplasmic reticular, nuclear, extracellular membrane and cytosolic fractions. This system provides a bridge from detection of proteins of interest found by analytical 2-D PAGE to preparative electrophoresis for isolation and sequencing by conserving the 2-D PAGE format. Elution of preparatively isolated proteins from electrotransfer membranes should also find uses in internal sequencing procedures, for raising specific antibodies or in designing oligonucleotide probes and primers to exploit available sequence information. Preparative 2-D PAGE has enabled the identification of some familiar and novel proteins relevant to carcinogenesis as discussed herein and will be useful in the exploration for new proteins involved in malignant transformation.

Features and characteristics of the present invention will be presented in following Examples which compare the preparative 2-D PAGE system of the present invention to an analytical 2-D PAGE procedure. The murine fibroblast C3H10T1/2 cells used in the Examples below were grown in basal medium Eagles (BME) medium supplemented with 2 mM glutamine, 10% heat-inactivated fetal calf serum (KC Biologicals) and 10 µg/mL gentamicin. Cells were washed three times with PBS, scraped in ice-cold BME and pelleted, and the medium removed. Cells were Dounce-homogenized in 5 volumes of 10 mM Tris, pH 7.0, containing 30 μg/mL aprotinin and 1 μg/mL leupeptin. After centrifugation at 1000×g for 10 minutes at 4° C., the pellet was rehomogenized, and after centrifugation, supernatant fractions were combined. PMSF was not included due to possible interference in protein sequencing. Samples were dialyzed overnight against water at 4° C. using 6–8 kDa molecular mass cut-off membrane (Spectrum, Houston, Tex.). Protein content was determined for dialyzed samples by the fluorescamine assay. Samples were subaliquoted and lyophilized to dryness.

EXAMPLE 1

In this Example, two-dimensional gel electrophoresis was performed as previously described for analytical conditions at ≤100 μg by Merrick et al. (*Appl. Theoret. Electrophoresis* 1992, 2, 177–187). Lyophilized protein was dissolved in urea lysis buffer composed of 9M urea, 4% NP-40, 2% carrier ampholytes (Servalyt pH 9–11, Serva, Westbury, N.Y.) and 1% diothiothreitol (DTT). Dissolved protein (2.5–5.00 μg/μL) was loaded in a 20 μL volume. IEF tube gels were cast to a height of 135 mm in glass tubes (150 mm×1.5 mm). Analytical IEF was conducted with an ISO-DALT tank (Model ID 125-1.5, Hoefer, San Francisco, Calif.) with the anolyte concentration at 100 mM phosphoric acid and catholyte at 20 mM sodium hydroxide. Samples were electrophoresed for a total of 11200 Vh with the final 2000 Vh being delivered over the last 2 hours. The pH gradient was determined from 0.5 cm sections of tube gel soaked in 1 m KCL. IEF tube gels were transferred into equilibration buffer and then placed on 10–16% acrylamide gradient slab gels. SDS-PAGE was conducted in a multiple gel tank (Model ID420, Hoefer) at 350 mA for 18 hours at 4° C.

EXAMPLE 2

In this Example preparative 2-D PAGE according to the present invention was performed with the objectives of increasing sample load and retaining resolution where analytical 2-D PAGE gel patterns served as the basis of comparison. The optimal operating conditions for preparative 2-D PAGE are described below. Optimization steps or varied parameters important to development of final running conditions are discussed below.

Dimensions of the IEF glass tube were 6 mm ID, 1 mm thickness, and 28 cm in length. Tube gels were prepared by aqueous dissolution of 9M urea, 4% carrier ampholytes (Resolyte 4–8, BDH Chemicals Ltd., Poole, England), 4.25% acrylamide, 0.25% Bis, 2% 3-[(3-cholamidopropyl)dimethylammonio]-1-propane sulphate (CHAPS) at 37° C., followed by degassing. Detergent and polymerization components were added for final concentration of 2% NP-40, 0.035% ammonium persulfate and 0.05% TEMED. A dialysis membrane (10 kDa cutoff) was secured with Parafilm around the outer edges of one IEF tube end in order to contain the gel solution. Gel solution was loaded with a glass pipette to a height of 22 cm and the top was then covered with Parafilm. IEF gels were aged overnight to allow for decomposition of reactive chemical intermediates after polymerization.

Figure 8:
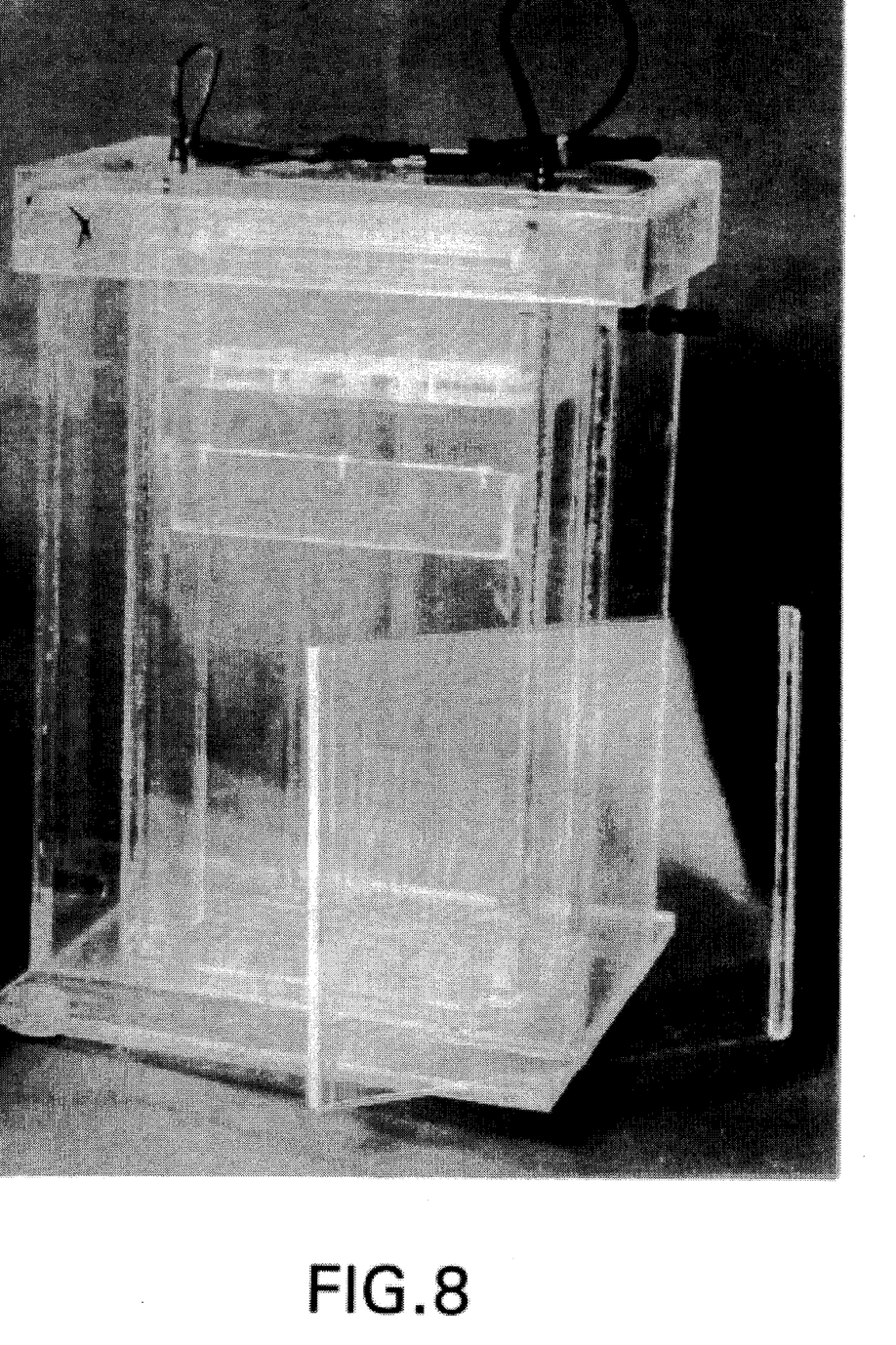
FIG. 8 is a perspective view of IEF chamber used according to one embodiment of the present invention.

FIG. 8 is a perspective view of IEF chamber used in this Example. The plexi-glass IEF apparatus was custom-designed to accommodate six preparative tube gels. The entire apparatus was enclosed in a plexiglass chamber with an upper and lower port on either side for connection to a recirculating temperature control pump (VWR Model 1166) to maintain the temperature at 18° C. The total volume of the enclosure chamber was 7 L. Female connections to the power supply (ISS Enprotech, Model ISS 500) were machined into the lid to make contact with male electrodes attached to the IEF chamber. The lid covered both the IEF apparatus as well as the enclosure chamber for circulating aqueous liquid (water).

Parafilm was removed from the top of IEF tubes which were then inserted through silicone rubber grommets (0.25 in ID, 0.5 in OD, Cole-Parmer Instrument Co., Chicago, Ill.) so that IEF tubes extended 2 cm into the catholyte chamber. IEF tubes were leak-tested prior to use. When leaks were found from continued use, two or three wrap-around layers with Duraseal (PGC Scientific, Gaithersburg, Md.) were sufficient to increase tube circumference until weak seals could be replaced at the end of the run.

The catholytic chamber was filled with 0.4 L of 45 mM sodium hydroxide which was pregassed immediately prior to use. The anolyte chamber contained 3 L of 15 mM phosphoric acid. A 25 μL gel overlay solution was used to protect the tube gel from catholyte during prefocusing and was composed of a 0.5M urea, 0.2% NP-40, 0.1% pH 9–11 carrier ampholytes, 5 mM DTT and 0.7M β-mercaptoethanol. Gels were prefocused for 5 minutes at 500 V.

Lyophilized protein was dissolved in 10 μg/μL of urea lysis buffer which contained 9M urea, 3.5% NP-40, 0.5% carrier ampholytes (Servalyt pH 9–11), 0.1% SDS, 0.5% CHAPS and 1% DTT. After prefocusing at 500 V for 5 minutes, samples were loaded into tube gels and electrophoresed at 18° C. for 10000 Vh at 500 V/h followed by an additional 2000 Vh for 2 hours at 1000 V/h to sharpen resolution. Thus, the total IEF run was conducted at 1200 Vh. The Ph gradient was determined from 0.5 cm sections measured in 1M KCl.

IEF tubes were extruded by flushing with water down the entire length of the tube gel edge after insertion of a 25 cm long, 22-gauge stainless steel needle attached to a 10 mL syringe. Tube gels were readied for SDS-PAGE in 100 mL of equilibration buffer containing 0.125M Tris, pH 6.8, 2.1% SDS, 10% glycerol, 0.133% DTT, o,05 mM thioglycolate and 0.0025% Bromophenol Blue. Tube gels were placed on a rotary shaker for 10 minutes.

Preparative gradient SDS-PAGE gels were cast in groups of eight using a gravity mixer (Electro-Neucleonics, Oak Ridge, Tenn.) set for a linear 10–16% acrylamide gradient.

Figure 9:
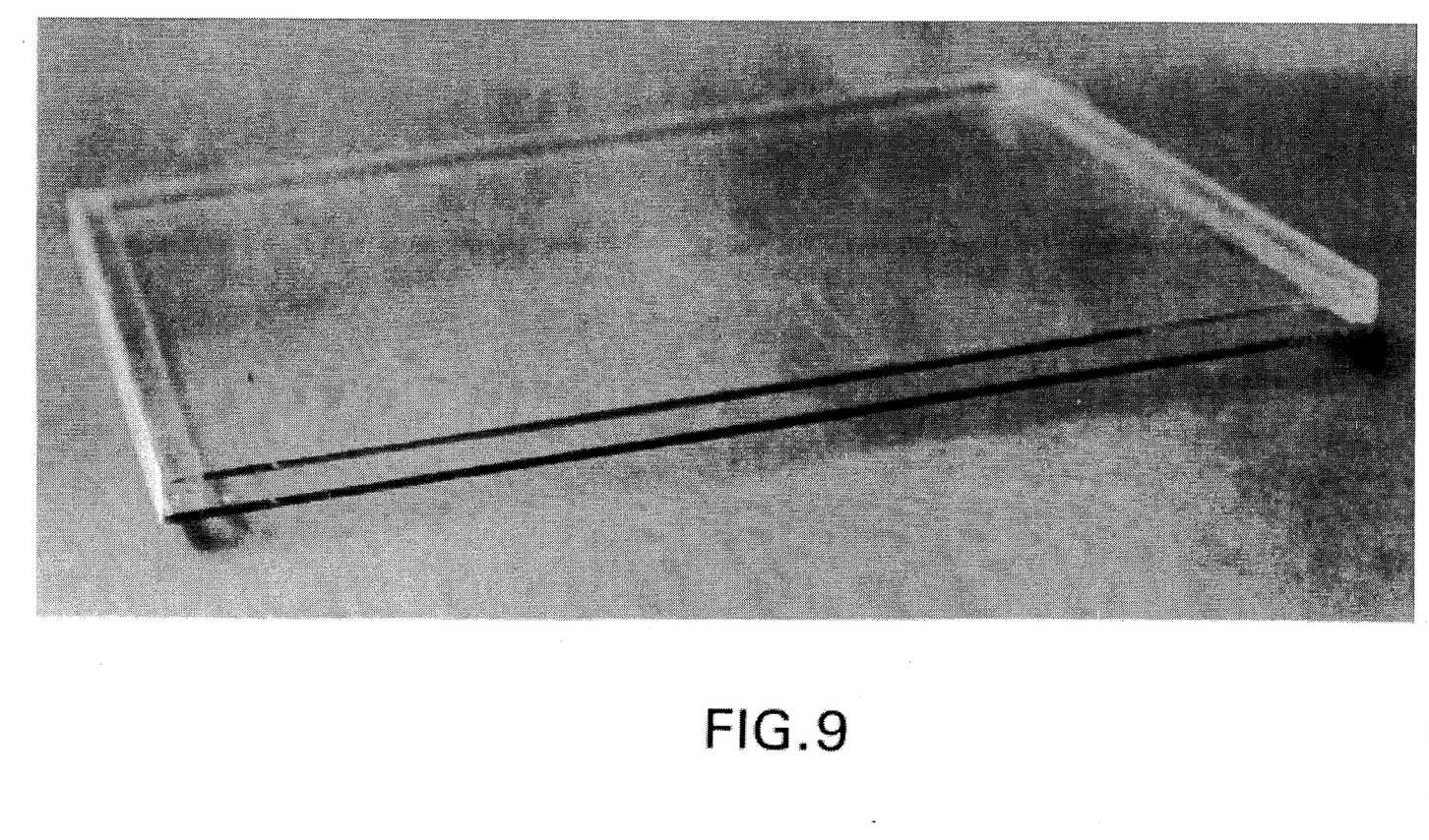
FIG. 9 is a perspective view of a preparative SDS PAGE glass mold unit according to one embodiment of the present invention.

FIG. 9 is a perspective view of a preparative SDS PAGE glass mold unit according to one embodiment of the present invention. Dimensions for the 6 mm ID glass plates for the second dimension were 20×25 cm using 1.5 mm thick glass (University Glassware, Chapel Hill, N.C.). Glass spacers at 20×0.75×0.6 cm were sealed on one plate at either end. The other glass plate was joined with adhesive by a 20×1×9 mm Neoprene strip to form a butterfly slab gel unit shown in FIG. 9. Gradient gels were poured to a height of 17 cm and aged overnight.

There were no special requirements for the SDS-PAGE tank other than accommodations of the physical dimensions of the second dimension gel unit and capability of holding multiple units. A multiple gel SDS-PAGE tank (Modol ID440, Hoefer) was filled with Tris-glyciine-SDS running buffer (Seprabuff, Enprotech, ISS, Natick, Mass.) containing 0.05M thioglycolic acid at 18° C. Preparative SDS-PAGE gradient slab gels were pre-run for 1 hour. The top surface of the slab gels were rinsed with distilled water just prior to loading IEF tube gels onto preparative slab gels. IEF tube gels were sealed to the top of the SDS-PAGE gels with molten agarose. Gels were run at 18° C. at 500 mA for 18 hours until tracking dye migrated out of the gel.

EXAMPLE 3

Figure 1A:
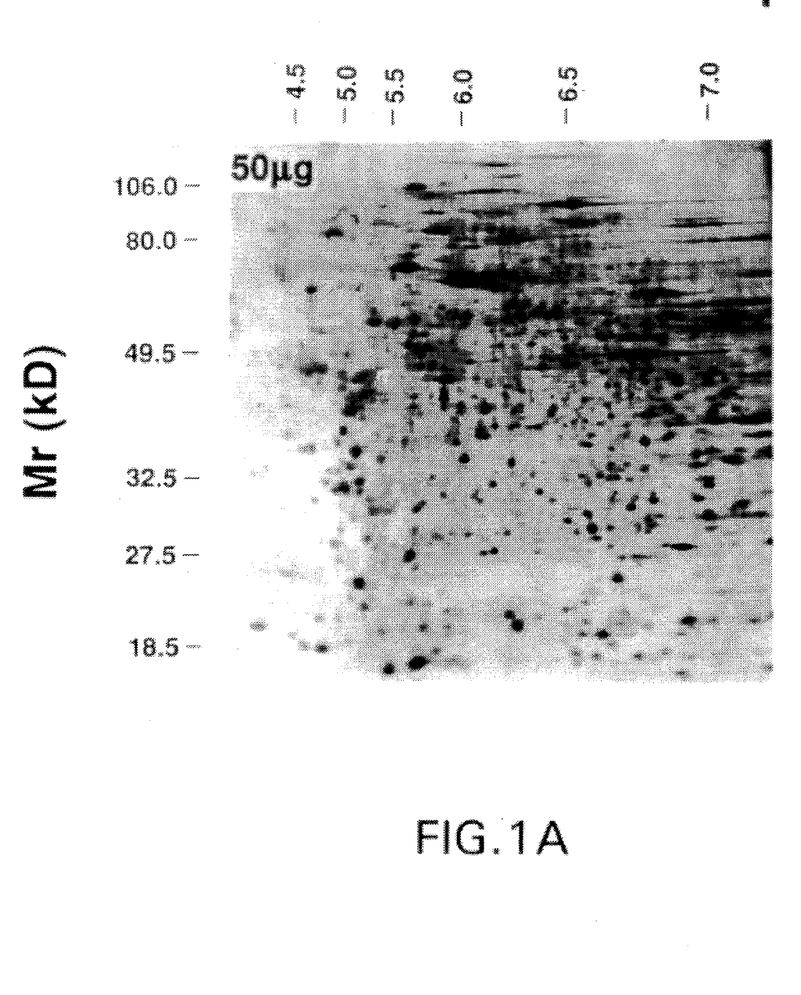
FIG. 1 is a comparison of protein staining sensitivity of colloidal gold and CBB on PVDF membranes.
Figure 1B:
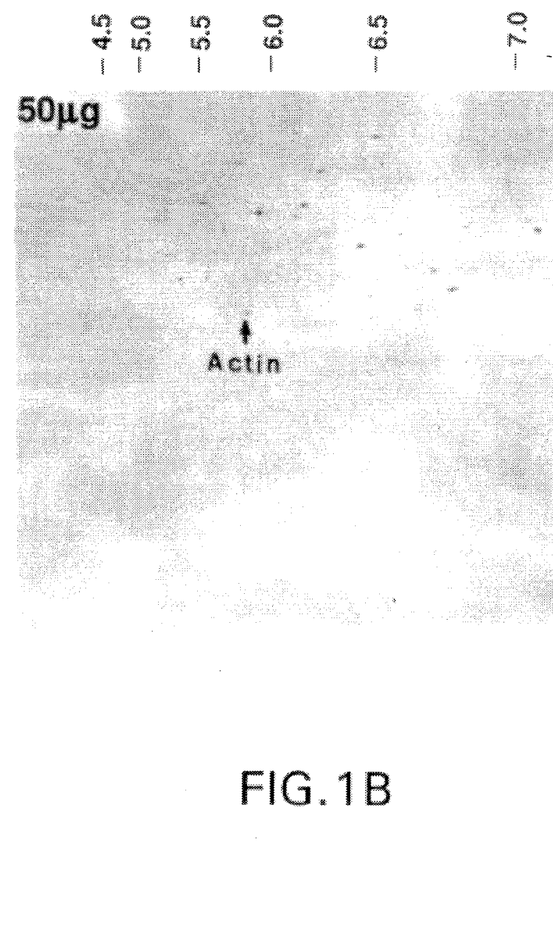

In this Example, electrophoresed samples from Example 1 were transferred from gels by semidry electroblotting into an 18×18 cm graphite electrode device (ISS Enprotech, Hyde Park, Mass.) to PVDF membranes (Immobilon, Millipore, Bedford, Mass.) at 1 mA/cm$_2$ for 1 hour. All electrode buffers contained 0.02% SDS, 0.05 mM thioglycolate and 20% v/v methanol in addition to the basic components. Anode 1 buffer contained 0.3M Tris, pH 10.4, while anode 2 buffer was at 0.025M Tris, pH 10.4. The cathode buffer was composed of 0.025M Tris and 40 mM e-amino-n-caproic acid (CAPS) at pH 9.4. Immobilon-P was used for colloidal gold staining (Bio-Rad, Richmond, Calif.) which was performed according to the manufacturer's protocol. Blots were washed 3 times for 20 minutes in 100 mL of Tris-buffered saline with 0.1% Tween 20 (TBS-T) followed by 3 rapid washes at 2 minutes each in reagent grade water to remove salts. Proteins were then stained in 50 mL of colloidal gold solution for 30–60 minutes. Color development was halted by transferal of the blot into water. FIG. 1 is a comparison of protein staining sensitivity of colloidal gold (left panel) and CBB (right panel) on PVDF membranes. Loads of 50 µg protein were separated by analytical 2-D PAGE, electroblotted and stained as described in this Example.

EXAMPLE 4

In this Example, slab gel samples from Example 2 were equilibrated in 10 mM CAPS, pH 11., 10% methanol and 0.02% SDS for 5 minutes prior to semidry electroblotting. Immobilon-PSQ was used for sequencing because of superior retention properties for proteins in the 18–100 kDa range. A 20×28 cm graphite electrode device (ISS, Enprotech) was used for protein transfer from one 6 mm thick preparative gel at 1.3 mA/cm$^2$ for 2 hours using the same buffers as the analytical system. Two transfer devices were used simultaneously for three runs to complete a complement of six preparative gels. Proteins were detected on Immobilon-PSQ with CBB staining as previously described by Patterson et al. (*BioTechniques* 1993, 14, 752–753. Stained proteins on PVDF membranes were excised, trimmed and destained in pure methanol. Membranes from two blots were inserted into a membrane blot cartridge and sequencing was performed on an ABI Model 473A protein sequencer (Applied Biosystems, Foster City, Calif.) using pulsed liquid flow.

The primary objectives in progressing from analytical to preparative 2-D PAGE were to increase sample load and preserve resolution in a manner compatible with protein sequencing. These considerations were driven by the limitations of analytical 2-D PAGE as exemplified in FIG. 1 in which the panel to the right shows the limited number of detected proteins and low staining intensity of CBB after electroblotting from a 2-D PAGE gel loaded with 50 µg of murine cytoplasmic protein. Colloidal gold staining of an identically processed 50 µg blot (left panel) shows a great many more patients (>1000) are actually present but are below the threshold of detection for CBB staining.

Initial attempts to combine multiple CBB-stained proteins from blots of analytical 2-D PAGE gels for sequencing were not successful. 100 µg was the upper limit for protein load on analytical 2-D gels; beyond this point, tube gel cracking and poor protein resolution occurred. Thus, the present inventors began to explore means for scaling up to preparative 2-D PAGE to obtain sufficient protein amounts detectable by reversible staining for sequencing.

The first objective was to design an IEF system capable of resolving increased protein loads. Enlargements of IEF gel dimensions was a first consideration. An increase in ID from 1.5 to 33 mm resulted in a fourfold increase in surface area while an increase to 6 mm ID produced a 16-fold change. If analytical 2-D PAGE produced a well-resolved pattern at 50 µg with an upper limit of 100 µg, a linear scale-up was expected to project a protein load capacity of 200–400 µg with a 3 mm ID IEF gel and an 800–1600 µg capacity for a 6 mm ID IEF gel.

In deciding between 3 mm and 6 mm ID IEF gels, the present inventors also considered the lower limit for protein sequencing to be about 20 pmole. This lower limit would be 1 µg for a 50 kDa protein. If 1 µg of protein is used as an estimate of the representative lower sequencing limit, then only the more abundant proteins of the cytosol have a reasonable likelihood of being sequenced. Isolation of 1 µg of protein from analytical protein loads of 50 µg are limited to proteins comprising at least 2% of the total. At a 250 µg load for a 3 mm ID preparative gel, proteins able to be sequenced should proportionately comprise $\geq 0.40\%$ of total protein. If electrophoresis of a 1 mg protein load on a 6 mm ID preparative system could accomplish separation of one thousand proteins at 1 µg each, then relative protein abundances would be at 0.1% of total.

In order to determine what number of proteins meet relative abundance criterion of 2%, 0.4% and 0.1% of total cytoplasmic proteins, image analysis was performed on silver-stained cytoplasmic protein patterns comparable to the 2-D PAGE gold-stained pattern in FIG. 1. Image analysis showed that only the actin series comprised 2% of the total protein. Forty proteins were at the $\geq 0.4\%$ abundance level while 272 proteins had relative proportions of $\geq 0.1\%$. These data suggested that a 6 mm preparative IEF gel would be the more rewarding prospect by almost sevenfold over a 3 mm IEF gel in providing threshold amounts of proteins for sequencing.

In order to provide for adequate resolution with larger protein loads, the length of the IEF tube gel was adjusted to 22 cm. As a result, the dimensions of the slab gel were set at 20×25 (h×w) to accommodate the length of the IEF tube gel and to produce a slab gel height comparable to the analytical slab gel.

In addition to dimensions of the slab gel, other considerations also included gel thickness and the acrylamide gradient. A linear 10–16% gradient for SDS-PAGE dimension produced a balanced spacing among proteins of varying mass as shown by the analytical 2-D PAGE pattern in FIG. 1. The same gradient was retained for preparative gels based on the projection that similar resolution in mass would occur under preparative conditions. The slab gel thickness was determined by the IEF tube gel size of 6 mm. Although 32 mm ID SDS-PAGE slab gels can resolve several mg of protein spread across a 22 mm length tube gel, initial test results were marred by poor 2-D PAGE resolution in mass due to distortion from inserting 6 mm IEF tube gels into 3 mm spaced slab gels. In order to overcome this problem, 6 mm ID butterfly slab plate units were designed which entailed the use of 1.55 mm thick glass.

The performance of preparative IEF was initially evaluated by comparing the formation of pH gradient with the tube gel. The duration of applied voltage was initially based upon analytical IEF conditions at 11225 Vh and catholyte and anolyte concentrations of 100 mM and 20 mM, respectively. Under these conditions for preparative IEF, proteins focused very poorly and pH gradients were non-linear, unstable and relatively basic compared to analytical IEF.

Several adjustments were made to improve preparative IEF, including a shift in the cathyolyte: anolyte ratio to 45 mM:15 mM, addition of SDS and CHAPS to the lysis buffer, inclusion of a gel overlay buffer and prefocusing. Under these adjusted conditions, a linear pH gradient was formed which was reproducible from run to run.

It was also discovered that increasing applied voltage time beyond 12000 Vh produced increasing cathodic drift and nonlinear pH gradients while applied voltage times below this duration were insufficient to set up a stable, linear pH gradient.

EXAMPLE 5

In this Example the effect of prefocusing times on pH of preparative IEF tube gels was studied. Of all the optimization steps for preparative IEF, prefocusing was of particular importance in formation of a linear pH gradient before application of sample. Without prefocusing, the lower two-thirds of the preparative IEF gel was excessively acidic at pH<3.

Figure 2:
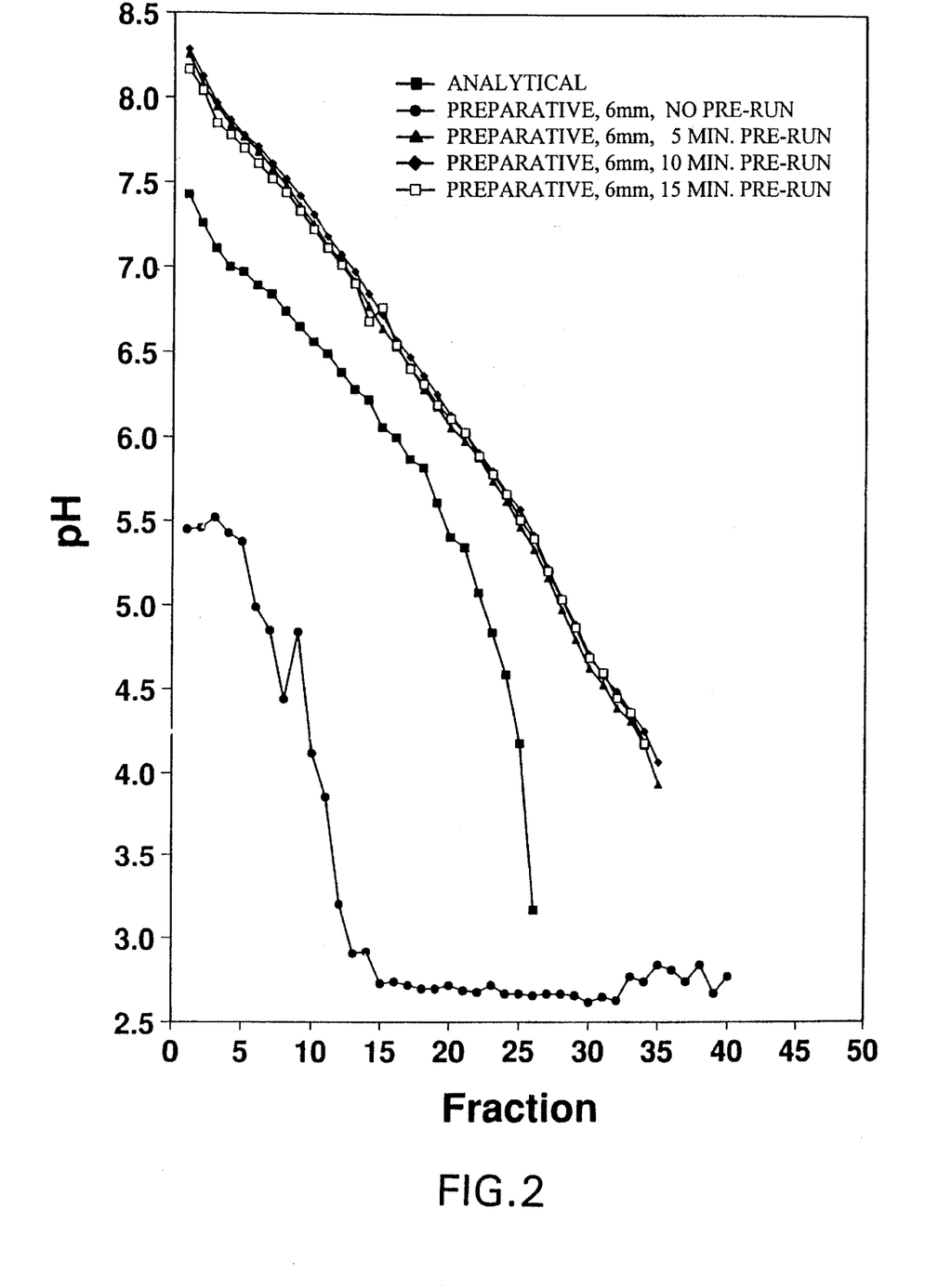
FIG. 2 shows the effects of prefocusing times on pH of preparative IEF tube gels (6 mm ID).

In this Example prefocusing at 500 V for times of 5, 10 or 15 minutes was preformed prior to complete IEF run at 12000 Vh. Preparative tube gels were 18 cm in length and 6 mm in ID. One tube gel was not prefocused as a control. FIG. 2 shows the effects of prefocusing times on pH of preparative IEF tube gels. As can be seen the different prefocusing time produced almost identical linear pH gradients, ranging from pH 4 to 8.2, and compared favorably to analytical IEF gels.

Figure 3:
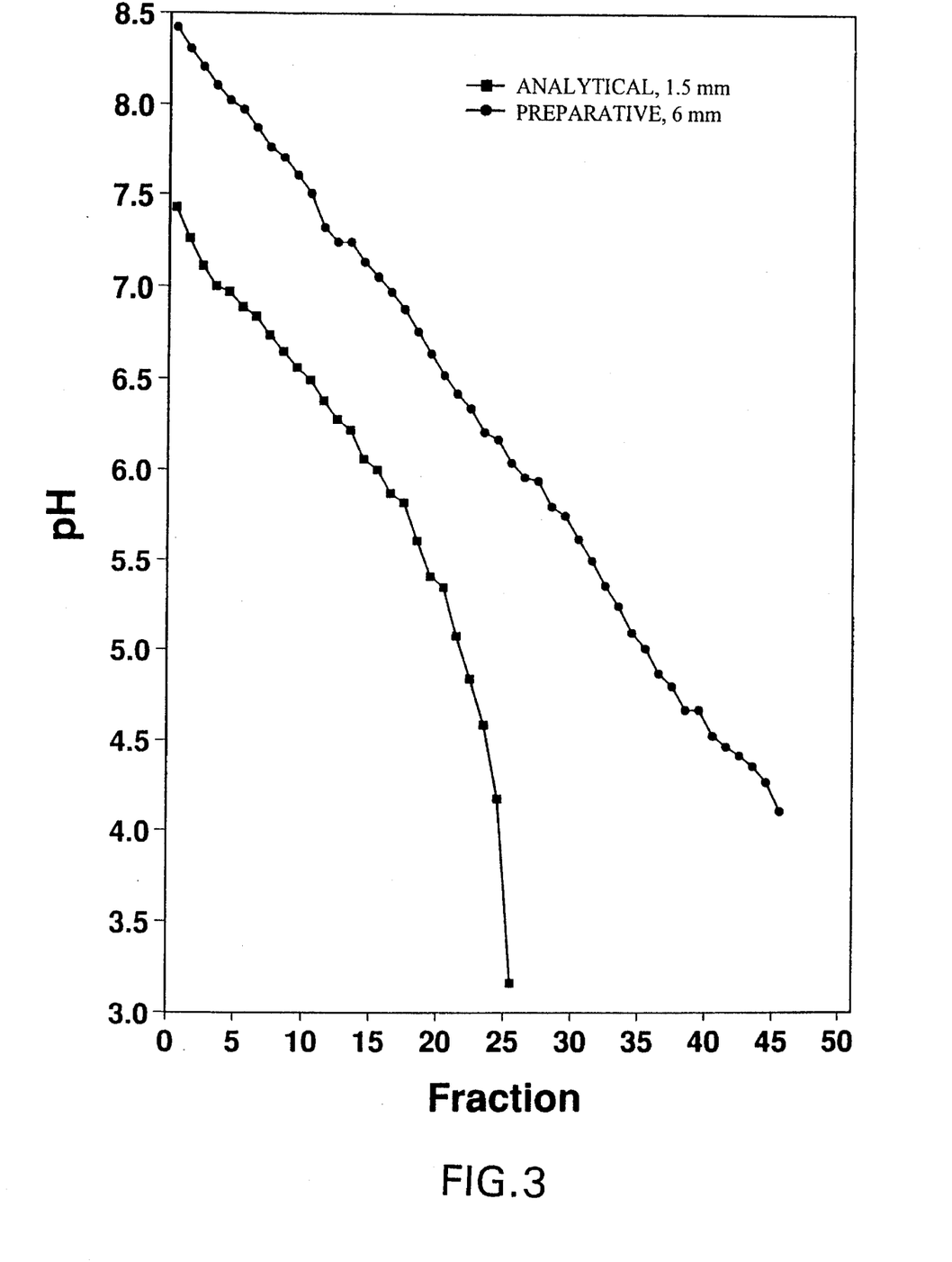
FIG. 3 shows comparisons of pH gradients of tube gels from analytical IEF (1.5 mm ID) and preparative IEF (6 mm ID) during optimal conditions.

Preparative IEF gels at 18 cm in length were used for generating data in FIG. 2. However, a final adjustment was made in the length of the preparative IEF gel to 22 cm to take maximal advantage of the available 23.5 cm space in the slab gel. FIG. 3 shows comparisons of pH gradients of tube gels from analytical IEF tube gels (1.5 mm ID) and preparative IEF tube gels (6 mm ID) during optimal conditions. Analytical tube gels were 133.5 cm long while preparative tube gels were 22 cm in length.

It was determined that a 5 minute prefocusing procedure was sufficient to ensure pH linearlity across the gel from about pH 4.2 to 8.5. By comparison, the pH gradient of the analytical IEF gel was linear from 7.4 to 5.5 but showed an increasing slope from pH 5.5 to 3.2. Thus, operating conditions were established for preparative IEF gels which produced a linear and reproducible pH gradient.

EXAMPLE 6

Figure 4A:
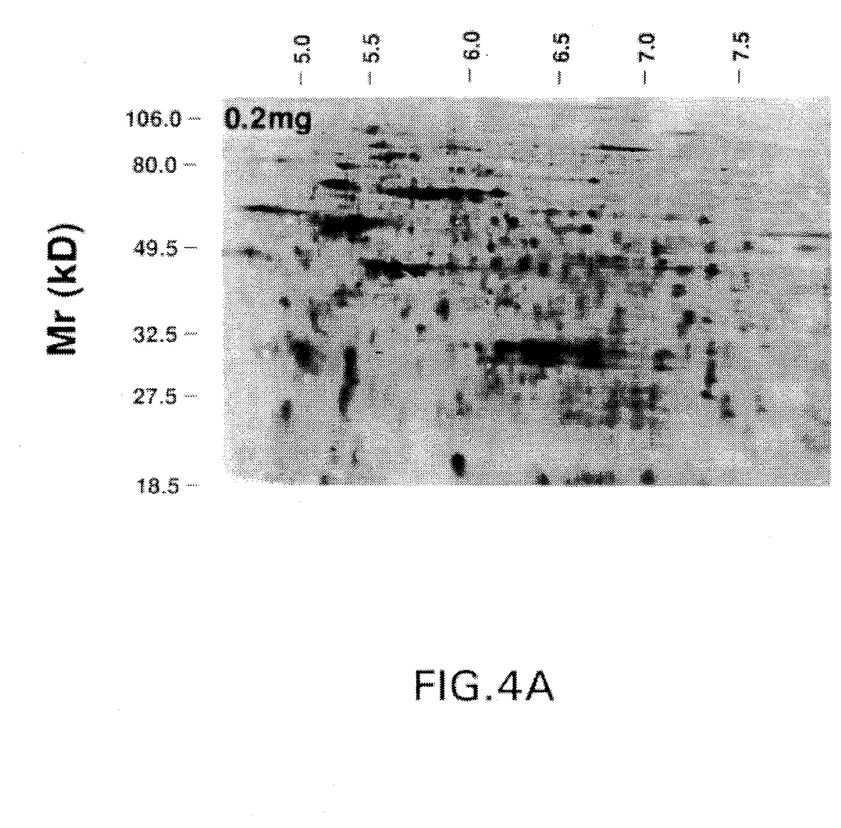
FIG. 4 shows visualization of blotted cytoplasmic proteins by colloidal gold or CBB staining after preparative 2-D PAGE.
Figure 4B:
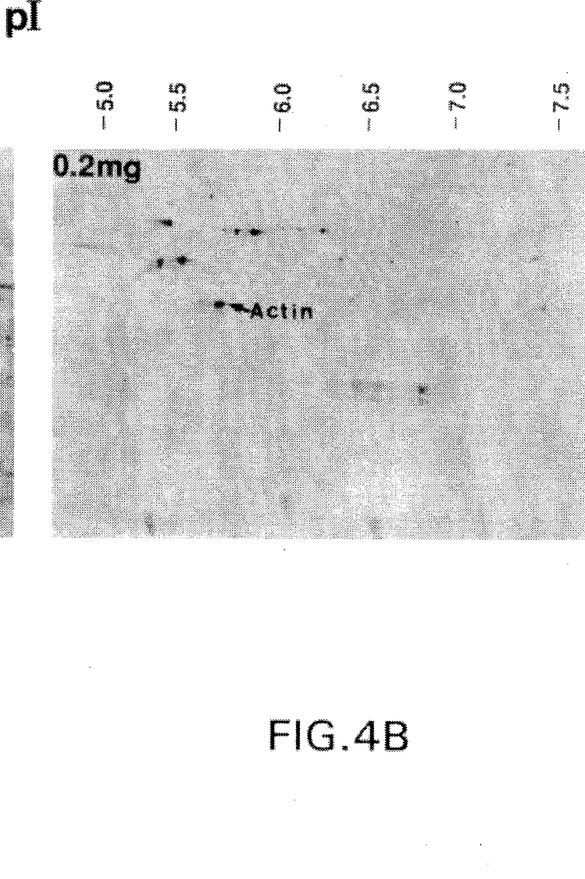
Figure 5A:
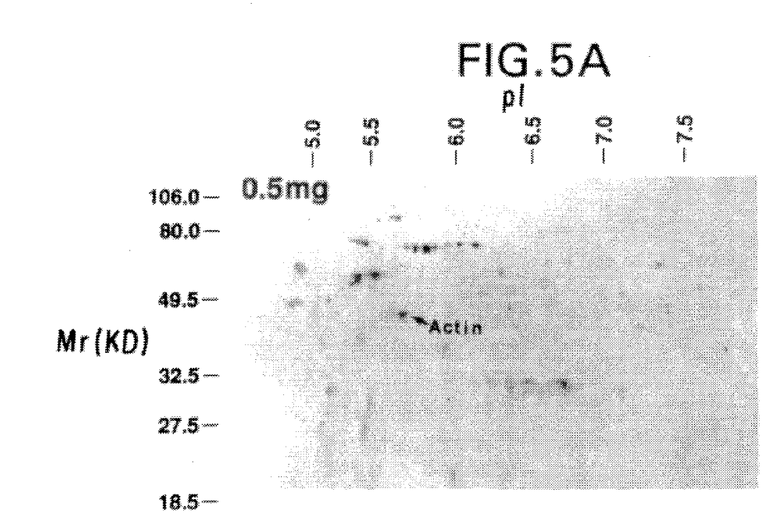
FIG. 5 shows the effects of increasing the amount of protein load (0.5–2 mg) upon resolution and staining intensity.
Figure 5B:
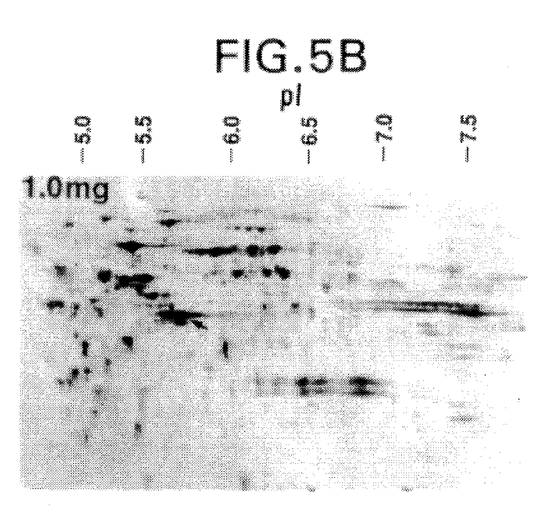
Figure 5C:
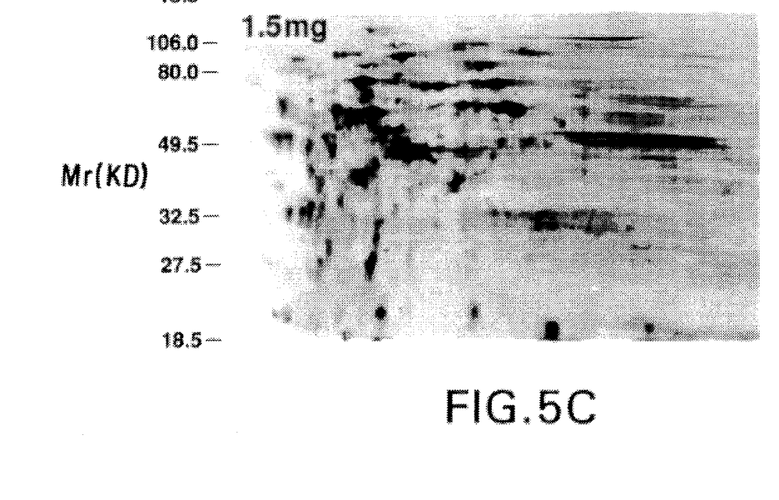
Figure 5D:
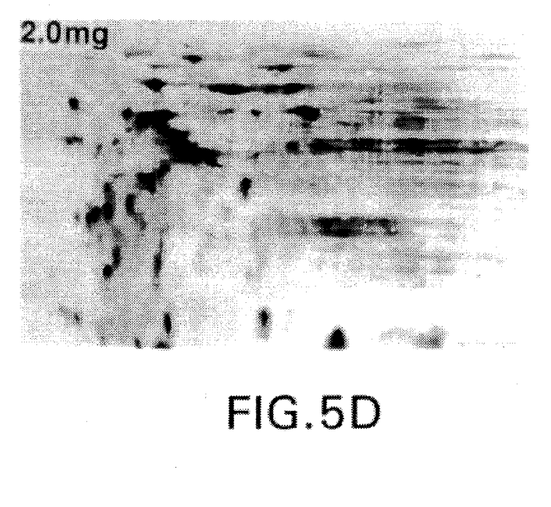

In this Example the performance of the preparative SDS-PAGE gradient gel was evaluated by separation of prestained standards from 18.5 to 106 kDa (BioRad, Hercules, Calif.). Separation of these protein standards by mass was comparable between analytical gels and preparative gels. FIG. 4 shows visualization of blotted cytoplasmic proteins by colloidal gold or CBB staining after preparative 2-D PAGE. Loads of 200 µg protein were separated by preparative 2-D PAGE, electroblotted onto PVDF membranes and stained.

FIG. 5 shows the effects of increasing the amount of protein load (0.5–2 mg) upon resolution and staining intensity. Murine cytoplasmic proteins were blotted onto PVDF after preparative 2-D PAGE and stained with CBB.

Performance of the preparative SDS-PAGE gradient gel was further evaluated by separation of prestained standards from 18.5 to 106 kDa (BioRad, Hercules, Calif.). Separation of these protein standards by mass was comparable between analytical gels (FIG. 1) and preparative gels (FIGS. 4 and 5). In addition, prestained standards served as visual indicator for the progress of SDS-PAGE separation and quality of electrotransfer onto PVDF membranes.

EXAMPLE 7

In this Example tests were performed to evaluate the limits of sample loading capacity and resolution in preparative 2-D PAGE gels. Cytoplasmic proteins from C3H10T1/2 cells were separated by preparative 2-D PAGE from 0.2 to 2.0 mg, electrotransferred to PVDF membranes and stained. The practical lower limit for sample load in preparative 2-D PAGE represents an amount yielding detectable proteins in greater abundance than maximal analytical loads which was 0.1 mg in the analytical system used during the course of the present invention. At about 0.1 mg CBB-stained proteins could be visualized after analytical 2-D PAGE separation of 50 µg proteins (see FIG. 1) which essentially did not change at the 100 µg level. FIG. 4 shows the practical lower limit for a sample load of 0.2 mg in preparative 2-D PAGE where fifteen prominent proteins were observed after CBB staining of PVDF membranes. In order to demonstrate that many proteins were present but undetectable by CBB dye, the same blot was completely destained in methanol and then gold-stained as shown in the adjacent panel in FIG. 4. Gold staining shows that proteins were focused between pI 4.5–7.5.

The upper limits of protein load using preparative 2-D PAGE were examined in the range of 0.5–2 mg of protein (FIG. 5). The number of detectable proteins was improved the most in the 1–2 mg range, in which CBB-stainable proteins numbered about one hundred for the C3H10T1/2 murine cytoplasmic preparation. Proteins were well resolved in an isoelectric range of 4.5–7.0 at the 1.0–1.5 mg loads. Protein resolution was limited to a pH range of 4.5–6.5 with a 2 mg protein load. When gels were CBB-stained after electrotransfer of 2 mg load gels, little detectable protein remained within the gel, which suggests that the applied current and time were sufficient for complete transfer. In addition, placement of an additional PVDF transfer membrane and filler beneath the PVDF membrane for analysis revealed minimal "blow-through" from applied current at 1.3 mA/cm2/h, as monitored by gold staining. Thus, the widest range of resolved proteins occurred at a 1 mg load where over 90 proteins were observed after CBB staining of PVDF transfer membranes.

EXAMPLE 7

In this Example number of prominent and well-resolved CBB stained proteins were subjected to amino-terminal sequencing to demonstrate that sufficient protein was available for analysis from a single preparative 2-D PAGE analysis according to the present invention. Six 1 mg samples of C3H10T1/2 cytoplasmic protein, were analyzed by preparative 2-D PAGE, electrotransferred and stained with CBB. Individual proteins were excised from two or three blots for analysis. Blots were inserted into a vertical flow blot cartridge and sequenced (ABI 473A Protein Sequencer). Each protein which could be sequenced was analyzed a second time to ensure accuracy.

Figure 6:
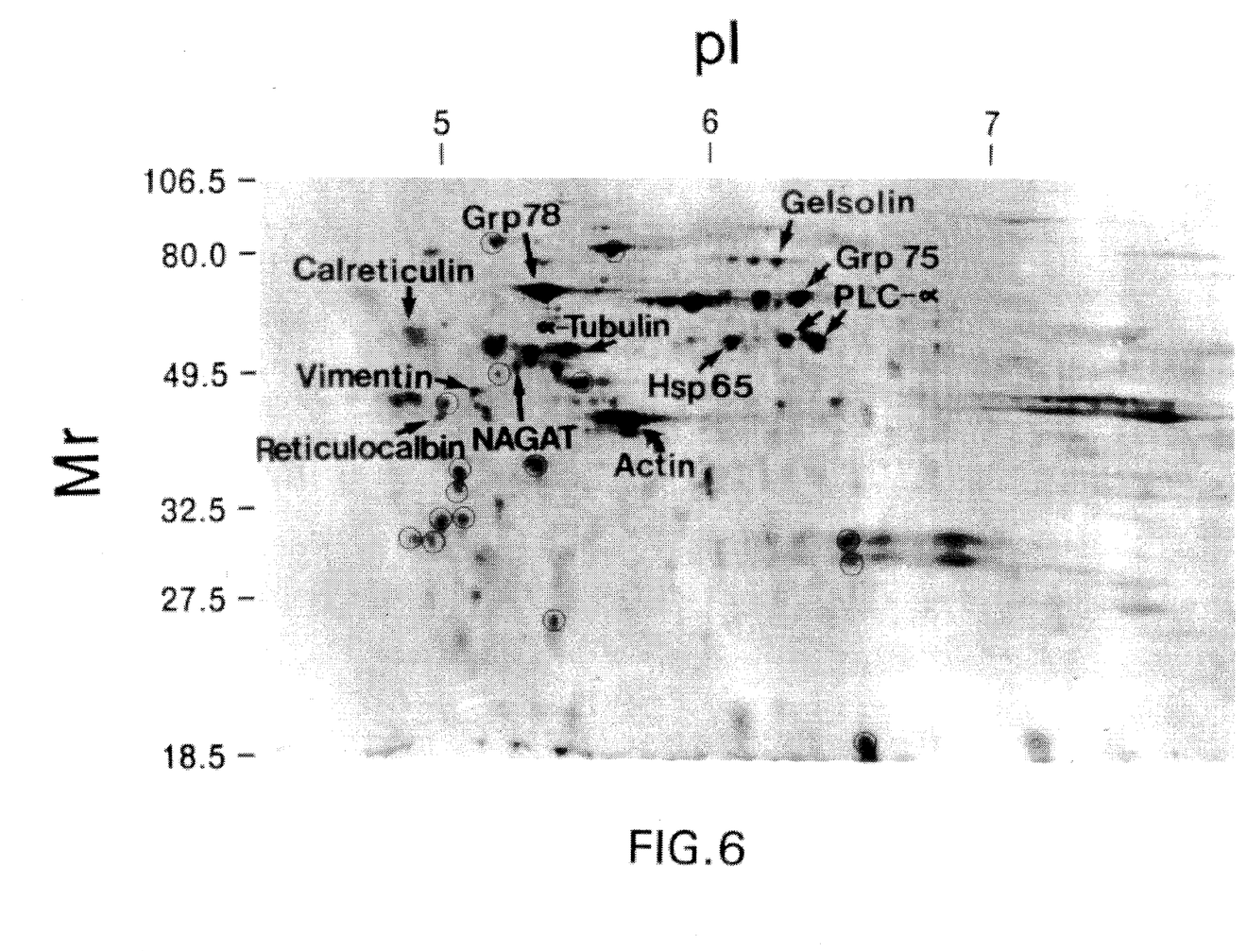
FIG. 6 shows the sequencing of major CBB-stained proteins separated by preparative 2-D PAGE.
Figure 7A:
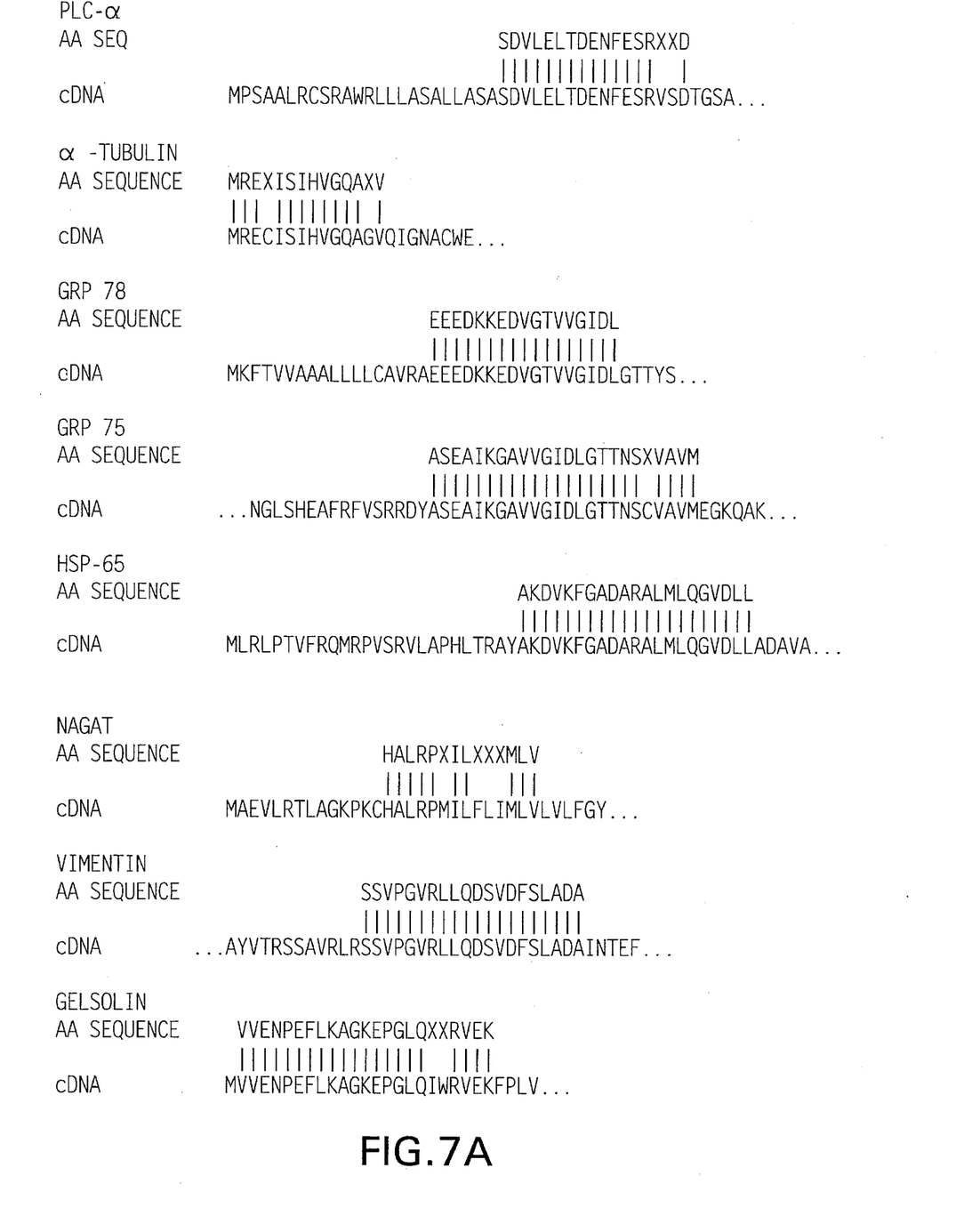
FIG. 7 shows the identification of sequenced murine proteins isolated from preparative 2-D PAGE gels. N-terminal sequences (AA sequence) derived from proteins indicated in FIG. 6 were aligned with amino acid sequences predicted from cDNA sequencing. All amino acid sequences were derived from murine cDNAs with the exception of NAGAT, which were derived from human cDNA, Most amino acid sequences begin several residues into the predicted sequence indicating the presence of a leader sequence. Note that PLC-α "A" and "B" share the same sequence. "X" represents an unidentifiable residue.
Figure 7B:
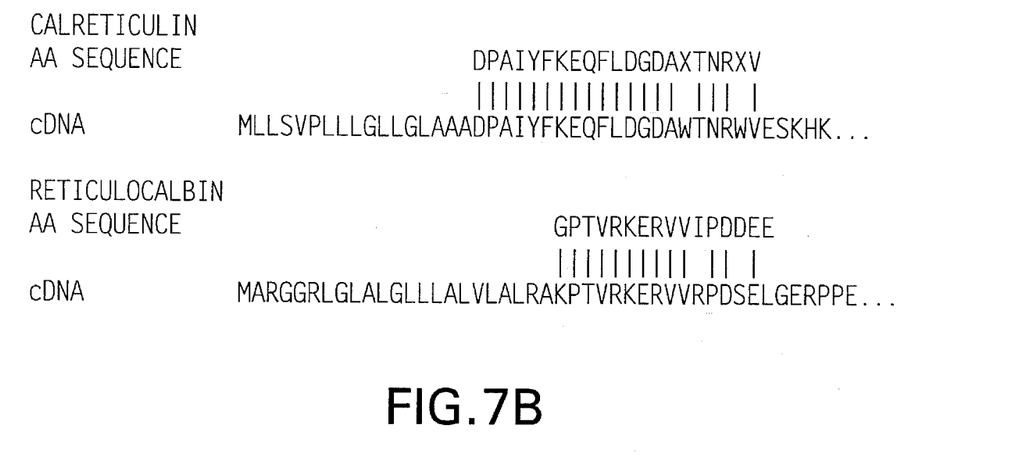

FIG. 6 shows the sequencing of major CBB-stained proteins separated by preparative 2-D PAGE. Proteins from which sequence information was obtained (Table 1) but could not be recognized by sequence alignment are indicated by arrows to their respective molecular masses (i.e. P19). Proteins which did not produce usable sequences are circled and are presumed to be N-terminal blocked. Identities were assigned on the basis of N-terminal sequence alignments with predicted amino acid sequences as seen in FIG. 7.

In FIG. 6 actin proteins are indicated for reference but were not sequenced since they are terminally blocked in most preparations. Seventeen proteins for which sequences could be obtained are indicated by the straight arrows. Alignment searches in automated databases revealed sufficient homology to assign identities indicated on FIG. 6. Sequences were also obtained from six proteins indicated by narrow arrows and are referred to by their relative $M_r$ (i.e. P19). Table 1 below shows the sequences from these proteins ranging from five to eleven residues which did not consistently align with amino acid sequences of known proteins in automated databases.

TABLE 1

Amino-terminated Sequences From Unidentified

| Proteins Isolated from Preparative 2-D PAGE | |
|---|---|
| P19 | WIGRW ... |
| P32 | MEDEJQDXI ... |
| P36 | HEEAELD ... |
| P46 | PKPPDRG ... |
| P48 | KYIXXDDVIEL ... |
| P50 | HSEPGGAY ... |

No sequence could be obtained from ten circled proteins and they were presumed to be N-terminal blocked.

FIG. 7 shows the identification of sequenced murine proteins isolated from preparative 2-D PAGE gels. N-terminal sequences (AA sequence) derived from proteins indicated in FIG. 6 were aligned with amino acid sequences predicted from cDNA sequencing. Most amino acid sequences begin several residues into the predicted sequence indicating the presence of a leader sequence. Note that PLC-α "A" and "B" share the same sequence. "X" represents an unidentifiable residue.

Protein sequences from the eleven identified proteins in FIG. 6 ranged from 14 to 24 residues in length and were aligned with amino acid sequences predicted for cDNA as shown in FIG. 7. The cDNAs were derived from murine excels with the exception of δ-N-acetylgalactosaminyl transferase (NAGA) which was only available from human cells. Most of the identified proteins except for α-tubulin and gelsolin contain an inferred leader sequence since the terminal residue is several residues away from the terminal methionine predicted by cDNA. These lead or signal sequences are consistent with sequences of about 20 amino acids in length observed for many proteins undergoing processing into their mature form. Vimentin and Grp 75, however, contain longer leader sequences of 58 and 46 amino acids in length, respectively.

The preparative 2-D PAGE system of the present invention is particularly useful for isolation and sequencing of C3H10T1/2 proteins as a means to identify proteins during carcinogenesis experiments. Centrifugal subcellular fractionation has been used to enrich cytoplasmic proteins containing organelles and soluble proteins, many of which are important in cell signaling pathways. For example, two 62 kDa proteins responding to serum-dependent growth and growth areas were recently detected by analytical 2-D PAGE in cytoplasmic fractions of dividing C3H10T1/2 cells Merrick et al. (*Biochem. Arch.* 1993, 9, 335–340). After isolation by preparative 2-D PAGE according to the present invention, these two proteins were identified by protein sequencing as isoforms of phospholipase C-α (PLC-α). PL-α enzymes are a family of cysotosolic and membrane-bound proteins which catalyze hydrolysis of inositol phospholipids to the second messengers, diacylglycerol and phosphoinositides which function in various signal transduction pathways. During the course of the present invention attention was focused on C3H10T1/2 cytoplasmic proteins as a subcellular compartment from which other proteins of interest to carcinogenesis might be found during experimentation in culture.

The limited sensitivity of CBB staining makes pooling of blotted proteins from analytical 2-D PAGE largely ineffective since so few proteins are stained. During the course of the present invention, it was discovered that separation of 50–100 µg of cytoplasmic protein by analytical 2-D PAGE produced only 10 CBB stainable proteins, despite the presence of about 1000 proteins detected by colloidal gold staining of the same blot. Therefore, initial considerations for preparative 2-D PAGE were driven by protein load capacity, particularly in the IEF dimensions since it is more capacity limited than SDS-PAGE. In order to increase the load capacity, it was necessary to increase the physical dimensions of the IEF tube gels and create a new IE chamber and slab gel unit to accommodate 6 mm tube gels. Additionally, several reagent adjustments were necessary, specifically in the composition of the IEF tube gel, sample buffer and anolyte and catholyte concentrations.

Protein solubilization and stability of the pH gradient were enhanced by adding two times the amount of soluble carrier ampholytes (4% pH 4–8) and nonionic detergent (2% NP-40 and 2% CHAPS) to the preparative IEF tube gels compared to analytical IEF gels. In the case of IEF gel detergents, a mixture of NP-40 and CHAPS provided better protein solubilization than 4% of either detergent alone. Use of alternate nonionic detergents such as n-octyl glucopyranoside, did not improve resolution. The addition of 0.1% SDS and 0.5% CHAPS to preparative sample dissolution buffer enabled protein solubilization up to 15 µg/µl. It was found that a 3:1 catholyte:anolyte ratio was most useful for preparative IEF to reduce the effects of cathode drift. Prefocusing, even for as short a period as 5 minutes, was requisite for successful preparative IEF. With those technical modifications, proteins were well focused after preparative 2-D PAGE in the pH range of 4.5–7.0 but less so at more basic isoelectric points despite the linearlity of the pH gradient up to pH 8.5.

According to the present invention, a one milligram load of uniformly distributed proteins could theoretically provide 1000 proteins in 1 µg amounts at a relative abundance of 0.1%. In reality, data from silver-stained 2-D PAGE gels showed that there were 272 cytoplasmic proteins with relative proportions of ≧0.1%. When preparative 2-D PAGE was performed, it was discovered that 6 mm IEF gels, unlike analytical 1.5 mm IEF gels, could accommodate up to 2 mg of cytoplasmic protein without gel breakage or major disturbance of the pH gradient. Practical concerns about deteriorating protein resolution above 1 mg made this the optimal load of choice for C3H10T1/2 cytoplasmic proteins using the current methodology. About 100 CBB-stained proteins were detected from 1 to 2 mg protein load using preparative 2-D PAGE, or about forty (40%) of the predicted number of C3H10T1/2 proteins at the 0.1% level. The lesser number of CBB-stained proteins on preparative 2-D PAGE blots compared to the number predicted by silver staining of analytical 2-D PAGE gels might be explained by the following reasons. The predicted number of 0.1% proteins is an estimate, based on silver staining of proteins which exhibit individual variation in staining intensity per amount of protein. This factor limits direct extrapolation of 0.1% abundance proteins detected by silver staining to the number of CBB-stained proteins. Moreover, incomplete focusing of basic proteins (>pI=7) in preparative gels detracts from the number of resolved proteins which could be observed in this region under analytical conditions. Despite these consideration, most CBB-stained cytoplasmic proteins were sufficiently well resolved between pH 4.5–7.0 under preparative conditions to allow for easy excision of individual proteins from PVDF transfer membranes for sequence analysis.

Several studies have examined optimization of blotting conditions for use of various transfer membranes for protein sequencing. Recent evaluations of various transfer membranes showed increased protein retention with high specific surface area and narrow pore sizes which are characteristic of new PVDF membranes, such as Immobilon-PSQ used here. A recently reported procedure to increase protein retention and detection of murine cytoplasmic proteins blotted onto Immobilon-PSQ over immobilon-P membranes using an improved CBB staining procedure was implemented (Patterson et al. *BioTechniques* 1993, 14, 752–753). Additionally, various precautions were taken to reduce amino-terminal blockage including aging of acrylamide gels and addition of a reducing agent to second-dimension running buffers and to membrane transfer buffers. Membrane electrotransfer time and current were adjusted for nearly complete removal of protein from 6 mm thick slab gels of the second dimension with minimal "blow-through" loss through the transfer membrane. Finally, use of a vertical-blot cartridge more easily accommodated protein punches from two to three blots for a more optimized solvent flow patten designed for protein sequencing from membrane supports. This precluded use of polybrene as required for applying protein samples to sequencing membranes for use in standard horizontal cartridges. These combined procedures contributed to consistent protein sequencing results during multiple runs to confirm each protein sequence.

The selection of 27 prominently stained cytoplasmic proteins yielded sequences from 17 proteins or two-thirds of the proteins examined. Of these 17 proteins, 11 were identified by alignment searches through GenBank/EMBL computerized databases. Some of these proteins provide integrity to cellular structure or the extracellular matrix such as gelsolin, α-tubulin and vimentin, while others, like Grp78, Hsp65 and Grp75, belong to the heat-shock class of proteins and have protective or cellular trafficking functions. Some sequenced proteins, like NAGAT and PLC-α have enzymatic roles and two identified proteins, calreticulin and reticulocalbin, serve as calcium binding proteins. Several of these proteins have only recently been identified by cloning and sequencing techniques, while six proteins from which only shorter amino acid sequences were obtained (Table 1) were not well-aligned in protein databases and await further efforts in establishing their identities as known or novel proteins.

Note that many of the sequenced proteins show apparent proteolytic processing in that the amino terminus obtained from protein sequencing was often several residues away from the methionine predicted by an ATG start codon from cDNA sequencing. These preliminary peptides often serve as signal sequences for intracellular targeting or as membrane anchoring units which aid in protein processing and function. The remaining ten proteins which were refractory to Edman degradation sequencing are presumed to be N-terminal blocked or contain insufficient amounts for signal generation. Sequential deblocking techniques for acetyl, formyl and pyroglutamyl modified amino-termini of blotted proteins often permit successful microsequencing of unknown proteins as evidenced by the recent report by Hirano et al. (*Electrophoresis* 1993, 14, 839–846). Alternately, internal sequencing strategies after chemical or enzymatic digestion should provide a ready means for obtaining sequence information from many of the proteins isolated here by preparative 2-D PAGE which were initially refractory to amino-terminal sequencing.

Specialized membranes composed of carboxymethylcellulose or cationic, charge-modified PVDF have been developed for high retention, but efficient elution of proteins. During the course of the present invention, high transferelution membranes for generation of internal cleavage fragments from blocked proteins isolated by preparative 2-D PAGE were evaluated. Several of the identified proteins have relevance for carcinogenesis studies such as the differential effects of serum-dependent growth or deprivation upon PLC-α-isoforms as already mentioned above.

A new heat shock 70 class protein has been recently cloned and sequenced from human and murine cells and has been termed Grp75, PBP74, CSA, and $p66^{mot-1}$ by different research groups. This protein shares the -IDLGTTNS- and -DLGGGTFD- consensus sequences characteristic of Hsp7-type proteins. The Grp75 designation of Morimoto's group (*GCG GenBank/EMBI*, Database, Madison, Wis., Acc. No. L15189) was chosen based on the shared motifs and similar characteristics with other glucose regulatory proteins. Recent immunohistochemistry studies show Grp75 is constitutively expressed in all tissues with primary localization to the mitochondria. Proteolytic processing of Grp75 occurs since a 46-residue amino-terminal signal peptide predicted by cDNA is absent from the mature protein which is also corroborated by the amino-terminus observed for Grp75 used in the present invention (see FIG. 7). Additional processing may also occur since 75 kD and 66 kD forms have been found.

Insights into the possible biological function and relationships to carcinogenesis are provided by Wadwha et al. (*J. Biol. Chem.* 1993, 268, 6615–6621) who showed that microinjection of anti-$p66^{mot-1}$ antibody into senescent mouse embryo fibroblasts transiently stimulated their cell division and produced morphological alternations, suggesting to them a cellular mortality-related function of $p66^{mot-1}$. The authors portray the relationship of $p66^{mot-1}$ to carcinogenesis as related to an escape from cellular senescence genes. Recent preliminary reports, however, show that Grp75 is not limited to primary, mortalized cells but is also found in immortabilized cells as well. The present inventors have isolated and sequenced Grp75 protein from the human tumor line HT1080 as well as from murine C3H10T1/2 immortalized cells. It is worth considering that processing of Grp75 to the $p66^{mot-1}$ form may be limited to primary or senescent cells and occur minimally in immortalized cells. Grp75 has also been linked with antigen processing by its ability to complex with various antigenic peptides. However, a specialized role for Grp75 in the immune system, in addition to recently proposed folding and assembly functions accorded to most chaperoning, is still in the early stages of exploration. Further study of Grp75, its proteolytic products, and proteins which form complexes with it will illuminate its relevance to carcinogenesis.

Reticulocalbin is a novel protein residing in the lumen of the endoplasmic reticulum, which was recently cloned and sequenced from a mouse teratocarcinoma cDNA library during screening of clones for glycoproteins using anti-lectin antibodies. The present inventors have been able to identify the presence of this protein in the cytoplasmic fraction of dividing murine fibroblasts after microsequencing from preparative 2-D PAGE blots. In their immunoblot analysis from gene-transfected murine host cells, Ozawa and Muramatsu (*Nature* 1990, 343, 133–139) showed an unmodified 44 kDa form of reticulocalbin, matching the $M_r$ molecular mass of the protein sequenced by the present inventors, and smaller amount of a glycosylated 46 kDa species of reticulocalbin. Although it is tempting to assign P46 (Table 1) as the glycosylated form since it migrates near reticulocalbin (FIG. 6), our amino terminal fragment is not related to the predicted amino acid sequence of this protein. Ozawa and Muramatsu recognize a signal sequence form which they predict cleavage between alanine-20 and leucine-21. However, on the basis of the amino terminal residue from the protein sequence prepared according to the present invention, the data suggest that cleavage occurs between residues alanine-23 and glycine-24. There was also a difference of the nature of the N-terminal amino acid, to which was assigned the first residue as glycine despite the presence of a weak signal of lysine in the same chromatogram. Some amino terminal processing may account for this difference. The remaining portion of the sequence prepared according to the present invention was virtually the same as the amino acid sequence predicted from cDNA. Distinguishing features of reticulocalbin are the occurrence of six repeats of a domain containing the EF-hand motif characteristic of high affinity calcium-binding proteins and also the presence of the HDEL version of the DKEL endoplasmic EF-hand calcium-binding protein super family, which includes calmodulin, troponin C and myosin light cahin. The EF-hand, so named from earlier work with parcalbumin by Kretsinger (*Crit. Rev. Biochem.* 1980, 8, 119–174), consists of a calcium-binding loop of 12 amino acids that is flanked by two α-helices. Upon binding with calcium, EF-hand proteins undergo a conformational change and consequently interact with their target proteins.

Although the functions of reticulocalbin are not defined, researchers speculate that it may be involved in a lumiunal retention mechanism of the endoplasmic reticulum for DKEL-terminate proteins in which calcium binding is intimately involved. Further clues to its function may come from identification of associated proteins and differing responses of reticulocalbin to calcium ion concentration within the endoplasmic reticular lumen.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

We claim:

1. An integrated method for separating complex protein mixtures which comprises the steps of:
   a) prefocusing an isoelectric focusing tube gel having a length of about 22 cm and an inside diameter of about 6 mm for a period of time sufficient to produce a linear pH gradient through said isoelectric focusing tube gel;
   b) loading said prefocused isoelectric focusing tube gel with a sample mixture of proteins;
   c) applying a voltage across said sample-loaded isoelectric tube to cause separation of said sample mixture along a first direction;
   d) transferring said sample mixture from step c) to a slab gel having dimensions of 20×25 cm.; and
   e) applying a voltage across said slab gel to cause separation of said sample mixture along a second direction.

2. A method for separating complex protein mixtures according to claim 1, wherein said sample mixture has a amount greater than 100 µg.

3. A method for separating complex protein mixtures according to claim 2, wherein said sample mixture has a amount greater than about 0.5 mg.

4. A method for separating complex protein mixtures according to claim 3, wherein said sample mixture has a amount of between about 0.5 to 2 mg.

5. A method for separating complex protein mixtures according to claim 1, wherein said prefocusing comprises applying a voltage of about 500 V for at least 5 minutes to said isoelectric focusing tube gel.

6. A method for separating complex protein mixtures according to claim 1, further comprising the steps of:
   f) transferring said sample mixture from step e) which has been separated to a transfer membrane; and
   g) staining said sample mixture from step e) which has been transferred to said transfer membrane.

7. A method for separating complex protein mixtures according to claim 6, further comprising the step of:
   h) subjecting said sample mixture from step f) which has been stained to protein sequencing.

8. In a two dimensional gel electrophoresis process involving the initial separation of proteins in an isoelectric focusing tube gel, the improvement comprising:
   prefocusing said isoelectric tube gel for a period of time sufficient to produce a linear pH gradient through said isoelectric focusing tube gel; and
   loading the prefocused isoelectric tube gel with between about 0.5 to 2 mg of a sample mixture of proteins.

9. In a two dimensional gel electrophoresis apparatus having a plurality of isoelectric focusing tube gels, an electrophoresis chamber for supporting said isoelectric focusing tube gels, a plurality of slab gel molds, and an electrophoresis chamber for supporting said plurality of slab gel molds, the improvement comprising:
   a plurality of isoelectric focusing tube gels having lengths of about 22 cm and inside diameters of about 6 mm; and
   a plurality of slab gel molds having dimensions of 20×25 cm.

10. An integrated method for separating complex protein mixtures which comprises the steps of:
    a) prefocusing an isoelectric focusing tube gel for a period of time sufficient to produce a linear pH gradient through said isoelectric focusing tube gel;

b) loading said prefocused isoelectric focusing tube gel with a sample mixture of proteins;

c) applying a voltage across said sample-loaded isoelectric tube to cause separation of said sample mixture along a first direction;

d) transferring said sample mixture from step c) to a slab gel; and e) applying a voltage across said slab gel to cause separation of said sample mixture along a second direction;

f) transferring said sample mixture from step e) which has been separated to a transfer membrane; and g) staining said sample mixture from step e) which has been transferred to said transfer membrane; and h) subjecting said sample mixture from step f) which has been stained to protein sequencing.

* * * * *